United States Patent [19]

Glassner et al.

[11] Patent Number: 5,063,156

[45] Date of Patent: Nov. 5, 1991

[54] PROCESS FOR THE FERMENTATIVE PRODUCTION OF ACETONE, BUTANOL AND ETHANOL

[76] Inventors: David A. Glassner, 4454 Satinwood Rd.; Mahendra K. Jain, 3950 Jonquil La., both of Okemos, Mich. 48864; Rathin Datta, 442 W. Melrose Ave., #3, Chicago, Ill. 60657

[21] Appl. No.: 516,618

[22] Filed: Apr. 30, 1990

[51] Int. Cl.$^5$ .......................... C12P 7/28; C12P 7/30; C12P 7/06; C12R 1/145
[52] U.S. Cl. .................................. 435/150; 435/151; 435/160; 435/162; 435/813; 435/842
[58] Field of Search ................. 435/50, 151, 160, 162, 435/813, 842

[56] References Cited

U.S. PATENT DOCUMENTS

| | | | |
|---|---|---|---|
| 4,520,104 | 5/1985 | Heady et al. | 435/160 |
| 4,521,516 | 6/1985 | Lemme et al. | 435/148 |
| 4,605,620 | 8/1986 | Andersch et al. | 435/160 |

FOREIGN PATENT DOCUMENTS 306138  8/1930  United Kingdom ................ 435/150

Primary Examiner—Herbert J. Lilling
Attorney, Agent, or Firm—Quarles & Brady

[57] ABSTRACT

A process including multistage continuous fermentation followed by batch fermentation with carefully chosen temperatures for each fermentation step, combined with an asporogenic strain of *C. acetobutylicum* and a high carbohydrate substrate concentration yields extraordinarily high butanol and total solvents concentrations.

4 Claims, 1 Drawing Sheet

PROCESS FOR THE FERMENTATIVE PRODUCTION OF ACETONE, BUTANOL AND ETHANOL

FIELD OF THE INVENTION

The present invention generally relates to fementation. More particularly, it relates to an improved fermentation process for the production of acetone, butanol and ethanol.

BACKGROUND OF THE INVENTION

The acetone/butanol/ethanol (ABE) fermentation process has received considerable attention in recent years as a prospective process for the production of commodity chemicals (butanol and acetone) from biomass.[1,2] The ABE fermentation is the most widely studied among the anaerobic fermentation processes and is a model for complex primary metabolism fermentations. Prior to World War II, butanol was produced primarily by fermentation. With the advent of cheaper synthetic butanol derived from petroleum feed stocks, the fermentation process became uneconomical.

Butanol production by fermentation continues to attract interest because it is potentially less expensive than production from petroleum and butanol is an industrially useful solvent with potential uses as a chemical feedstock or liquid fuel. Butanol can also be used as a solvent in enhanced oil recovery. It has been estimated that if butanol were used in tertiary oil recovery for 5% of the current United States consumption that an additional 2 to 4 billion pounds per year would be required. This is 2 to 4 times the current United States use level of n-butanol.

The acetone-butanol-ethanol fermentation is usually carried out at 35°–37° C. using spore forming *Clostridium acetobutylicum*. Several solvent-yielding fermentation processes have been described using batch or continuous culture,[3,4,5] chemostats with cell recycling[6] or immobilized cell systems.[7] These processes yield butanol, acetone and ethanol in a ratio of 6:3:1.[8] Mixed solvent yields of 29–33% of fermentable carbohydrate have been reported in the literature.[9] A total solvent concentration of about 16–20 g/L and a butanol concentration of about 10–12 g/L are generally the upper limits because of the toxicity of the butanol produced.[10]

When the *C. acetobutylicum* is grown in a chemostat, different proportions of acids and solvents may be produced depending on the dilution rate and the medium composition. It is also known that changing the fermentation temperature can affect butanol and solvent yield. In batch fermentation experiments conducted with three different solvent-producing strains, solvent yields remained fairly constant at around 31% at 30 and 33° C., but decreased to 23–25% at 37° C.[11] Similar results were obtained in a more recent study with *C. acetobutylicum* NCIB 852 in which solvent yields were found to decrease from 29% at 25° C. to 24% at 40° C., although the fermentation time decreased as the temperature was increased.[12] The decrease in solvent yield appeared to reflect a decrease in acetone production, while the yield of butanol was unaffected. This is in contrast to earlier findings in which an increase in the butanol ratio was obtained by decreasing the temperature of *Clostridium saccharo-butyl-acetonicum-liquefaciens-delta* fermentation from 30° to 24° C. after 16 hours.[13] However, all these fermentations were carried out under batch conditions only. It is clear from the prior art that the effect of fermentation temperature on the yield and concentration of solvents cannot be predicted prior to doing the experiments.

To achieve an improved fermentation process the concentration, yield, and productivity of solvents must be improved.

BRIEF SUMMARY OF THE INVENTION

It is the primary objective of the present invention to disclose an improved ABE fermentation process.

It has now been discovered that by using asporogenic strains of *C. acetobutylicum*, in a multistage, temperature programmed, combined continuous and batch fermentation process an extremely high substrate concentration can be fermented (about 60 to about 120 g/L); the byproduct formation can be reduced (more butanol and less butyric and acetic acids); and the solvent concentration can be unexpectedly high (e.g. above 20 g/L butanol and above 30 g/L solvents).

In the method of the present invention, an asporogenic strain capable of producing butanol, acetone and ethanol is first cultured on a medium containing assimilable carbohydrate and other growth nutrients under optimal conditions (temperature about 33° to about 38° C. and pH of about 4.8 to about 5.5 for about 3 to about 7 hours) in the first of at least two continuous fermentors connected in series to produce maximum growth of microorganism and organic acids, continuing the fermentation in a second and any additional continuous fermentor at about the same or lower temperature (e.g. about 24° to about 36° C. for about 4 to about 18 hours) upon a substrate until butanol, acetone and ethanol are formed, followed by a batch fermentation of the broth at about the same or a lower temperature (about 24° to about 30° C.) to complete the fermentation.

Only the unique combination of the robust asporogenic strains and a multistage continuous and batch fermentation with unique temperature programming provides the high butanol and solvent concentrations of this new process invention.

DESCRIPTION OF THE PREFERRED EMBODIMENT

Figure 1:
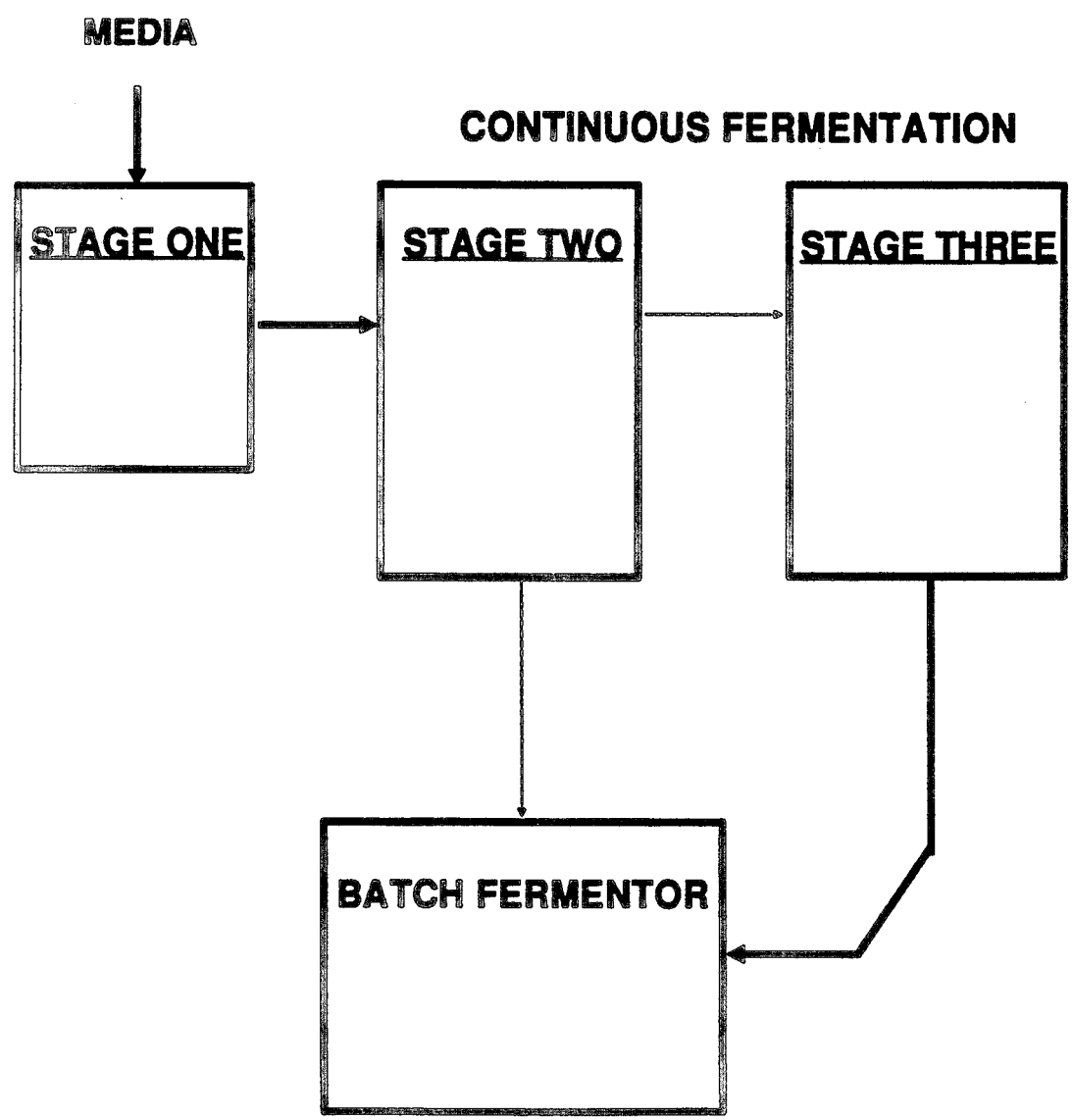
FIG. 1 shows the preferred fermentation vessel configuration and the process flow pattern.

In the preferred embodiment of the invention, the microorganisms employed are asporogenic *C. acetobutylicum* strains. One such strain (ATCC 39236) is described in detail in U.S. Pat. No.4,521,516. Another such strain (ATCC 55025) has been made in our laboratory.

The fermentation process of the present invention comprises first a multi-stage continuous fermentation followed by the batch fermentation of one or more of the fermentation broth(s) from the continuous stages.

In the preferred embodiment of the fermentation process, the first stage of the continuous fermentation is carried out at about 36° C. with a residence time of about 3 to about 7 hours, preferably about 4 hours, to partially convert the assimilable carbohydrate into organic acids, and the second stage of the continuous fermentation is at about 30° C. to about 36° C. with a residence time of about 7 to about 10 hours, to convert more of the carbohydrate into organic acids and to convert some of the organic acids into the desired solvents. The second stage is followed by either a batch fermentation at about 24° to about 30° C. until solvent production is complete (about 48 hours) or a third stage continuous fermentation at about 27° C. to about 36° C. with a residence time of about 7 to about 10 hours followed by batch fermentation at about 24° C. to about 30° C. until solvent production is complete (about 24 hours). The third stage continuous and the batch fermentation(s) usually finish the conversion of carbohydrate and organic acids to solvents. Additional fermentors are desired for continuous fermentation if the substrate concentration is very high (>100 g/L) and if the total residence time in preceding continuous fermentors is less than 15 hours.

During the process the pH is controlled at about 5.0 in only the first stage; it is not controlled in subsequent continuous or batch stages. The preferred medium or substrate is a low cost mixture of a starch hydrolysate, corn steep liquor, and corn gluten with a total carbohydrate concentration of about 85 to 90 g/L and the asporogenic strains of C. acetobutylicum disclosed herein are the preferred microorganisms.

The preferred process can result in butanol productivity of about 0.33 to about 0.35 g/L/hr and a solvent productivity of about 0.45 to about 0.53 g/L/hr. The butanol concentration ranges from about 16.5 to about 20.2 g/L. The total solvent concentration is from about 25.2 to 29.6 g/L (80-85 g/L substrate). The yield of butanol from the carbohydrate upon complete utilization is about 25% or more by weight and the total solvent yield can be 38% by weight or more. The process yields extraordinary high product concentrations at a good fermentation solvent productivity.

The high yield, high productivity and high solvent concentrations produced by the process of the present invention represents a greatly improved ABE fermentation compared to the prior art. The economics of solvent production by fermentation are much better with this invention. In addition, the method of the present invention utilizes very low cost media and capital costs are minimized by the simple process configuration. Furthermore the optimal process conditions include the lowering of the fermentation broth temperature to 30° C. or lower for the batch fermentation. If desired, a new separation process, pervaporation, may be integrated with the fermentation to help achieve this temperature reduction.

The fermentation process as seen in FIG. 1 consists of stage one, stage two and stage three continuous fermentors connected in series and batch fermentors for the effluents from the second and third stage continuous fermentors.

The preferred hydrolytic retention times in the fermentors are the following:

| Stage One | about 4.0–6.7 hr |
| Stage Two | about 7.5–16.7 hr |
| Stage Three | about 7.5–16.7 hr |
| Total Continuous | about 11.5–40 hr |
| Batch Fermentations | about 24–72 hr |
| Total Process | about 48–95.3 hr |

The fermentation medium may be any acceptable biomass which provides the necessary assimilable carbohydrate and growth nutrients for the organism to produce high yields and concentration of butanol and total solvents. Especially preferred is a medium containing about 80 to about 90 g/L of a starch hydrolysate, about 7 to about 12 g/L of corn steep liquor (CSL), about 7 to 12 g/L of gluten and about 5 ppm of $FeSO_4$ or an equivalent iron source.

EXPERIMENTAL WORK

The following is a brief description of the experimental work that was conducted to define and illustrate the invention.

Fermentation Parameters

Stage one was conducted in a New Brunswick Bioflo C30 continuous fermentor with 400 ml working volume maintained at 36° C. The pH was controlled between 5–5.2 with 4N solution of NaOH and 200 rpm agitation.

Stages two and three were conducted in similar Bioflo C30 fermentors with 1-liter working volumes. The stage two and three temperatures were maintained at 30°–36° C. and 27°–36° C., respectively. The fermentations in stage two and three were self-buffering and required no pH control. Agitation was set at 200 rpm.

In the batch fermentors, 100 ml aliquots of stage two and three effluents were fermented between 24° C. to 30° C. The batch completion fermentations were conducted in serum vials without agitation.

Fermentation Medium

The composition of the fermentation feed mediums for the continuous fermentors (Stages 1 to 3) were one of the following:

| Starch hydrolysate (Maltodextrin M-100) | 60 g/L | 80 g/L | 90 g/L |
|---|---|---|---|
| Corn Steep Liquor, CSL | 7.5 g/L | 10 g/L | 11.3 g/L |
| Gluten | 7.5 g/L | 10 g/L | 11.3 g/L |
| $FeSO_4$ | 5 ppm | 5 ppm | 5 ppm |

In each case the pH of the medium was adjusted to 5.2 with concentrated NaOH before sterilization. The medium was prepared in 12-liter carboys with the CSL and gluten sterilized separately.

Inoculation Procedure

Two asporogenic mutant strains (ATCC 39236 and ATCC 55025) and one sporeforming parent strain of C. acetobutylicum (ATCC 4259) were evaluated in different fermentor configurations.

The mutant strains were maintained in active phase in tubes containing starch hydrolysate (60 g/L), commercially available corn steep liquor (10 g/L dry basis) and gluten 10 g/L dry solids; the pH was adjusted to pH 5.4 with NaOH. Fifty ml of medium reduced with 0.025% cysteine-sulfide was inoculated from a fresh stock culture and incubated anaerobically for twelve hours. This 50 ml was used to seed 350 ml of medium in stage one which had been previously sparged for 30 min with nitrogen. Medium flow for a dilution rate of $0.25^{-1}$ hr was started after the pH dropped in the fermentor from 5.5 to 5 (about 5 hours after inoculation). The sporeforming strain was also grown and inoculated using same procedure except that the inoculum was grown in media that contained only 20 g/L starch hydrolysate substrate.

Analysis

Samples were taken daily from all three stages and from the batch fermentations of stage two and three effluents. Samples were analyzed for fermentation products by high pressure liquid chromatography (HPLC) and for residual carbohydrate by a YSI glucose analyzer after an enzymatic digestion of the carbohydrate.

Seven experimental examples are presented. In three of the examples, sporeforming *C. acetobutylicum* (ATCC 4259) and the asporogenic strains were used. In four examples, only the asporogenic strains of *C. acetobutylicum* were used. The fermentation equipment in each example consisted of continuous fermentors in series followed by batch fermentors for the completion of the fermentation of the effluents from the second or third stage fermentors. The differences between the examples were in the dilution rate used in each continuous fermentor and the fermentation temperatures. The batch completion fermentations of the effluents from the second and third stage continuous fermentor were also done at various temperatures. The reaction conditions for the examples are summarized in Table 1.

TABLE 1

Summary of Continuous Multistage Fermentation Processes with *Clostridium acetobutylicum*

| Examples | Stage 1 | Stage 2 | Stage 3 |
|---|---|---|---|
| 1. Sporeforming strain (ATCC 4259) Asporogenic strain (ATCC 55025) | | | |
| Temperature (°C.) | 36 | 36 | 36 |
| pH | 5.0–5.2 | not controlled | not controlled |
| Residence Time (hrs) | 4.0 | 7.5 | 7.5 |
| 2. Asporogenic strain (ATCC 55025) | | | |
| Temperature (°C.) | 36 | 36 | 36 |
| pH | 5.0–5.2 | not controlled | not controlled |
| Residence Time (hrs) | 4.0 | 7.5 | 7.5 |
| 3. Asporogenic strain (ATCC 39236) | | | |
| Temperature (°C.) | 36 | 36 | 36 |
| pH | 5.0–5.2 | not controlled | not controlled |
| Residence Time (hrs) | 6.7 | 10 | 10 |
| 4. Asporogenic strain (ATCC 39236) | | | |
| Temperature (°C.) | 36 | 36 | 36 |
| pH | 5.0–5.2 | not controlled | not controlled |
| Residence Time (hrs) | 6.7 | 16.7 | 16.7 |
| 5. Sporeforming strain (ATCC 4259) Asporogenic strain (ATCC 55025) | | | |
| Temperature (°C.) | 36 | 36 | 30 |
| pH | 5.0–5.2 | not controlled | not controlled |
| Residence Time (hrs) | 4.0 | 7.5 | 7.5 |
| 6. Sporeforming strain (ATCC 4259) Asporogenic strain (ATCC 39236) | | | |
| Temperature (°C.) | 36 | 30 | 27 |
| pH | 5.0–5.2 | not controlled | not controlled |
| Residence Time (hrs) | 4.0 | 10 | 10 |
| 7. Asporogenic strain (ATCC 39236) | | | |
| Temperature (°C.) | 36 | 30 | 27 |
| pH | 5.0–5.2 | not controlled | not controlled |
| Residence Time (hrs) | 4.0 | 12.0 | 11.5 |

After the establishment of steady-state conditions in the three continuous fermentors, aliquots from the second and third stages were fermented under batch conditions to completion. Steady-state conditions for the three stages and the results obtained after batch fermentation are presented for each process. The batch fermentations of the stage two and stage three effluents were incubated at either 24° C., 27° C. or 30° C.

EXAMPLE 1

Continuous Fermentation

The sporeforming and the asporogenic strains of *C. acetobutylicum* were compared in the multistage continuous fermentation configuration in terms of butanol and total solvent concentrations and solvent productivity rates. The fermentation process equipment consisted of three continuous fermentors (CSTR) in series with respective dilution rate of 0.25, 0.135 and 0.135 $h^{-1}$ for stage 1, stage 2 and stage 3. Stage 1 continuous fermentor was New Brunswick Multigen fermentor with 400 ml working volume. The pH was controlled at 5.1±0.1 with 4N NaOH at 200 rpm agitation. Stage 2 and 3 were multigen fermentors with 1-liter working volumes. The temperatures in all the stages were maintained at 36° C. The fermentation in stage 2 and 3 were self-buffering and required no pH control. Agitation was set at 200 rpm.

The results presented in Table 2 represent the average of at least 4 observations after the steady-state. Only acids were produced in stage 1 with no detectable production of butanol, acetone or ethanol. However, stage 2 data show that butanol and total solvent concentrations produced by asporogenic mutant strain were higher by 41–45% and this was repeated in stage 3. The solvent productivity rates in stage 2 (0.90 vs 0.63 g/L hr, asporogenic vs sporeforming strain) as well as stage 3 (0.95 vs 0.70 g/L hr, asporogenic vs sporeforming strain) also show that asporogenic strain has better fermentation rate. The results indicate that the asporogenic strain performs better in a multistage continuous fermentation system when compared with the sporeforming strain in terms of butanol and total solvents concentrations and solvent productivity rates.

TABLE 2

Comparative Performance of Sporeforming (ATCC 4259) and Asporogenic Strain (ATCC 55025) of *C. acetobutylicum* (Multistage Continuous Fermentation at Steady-State)

| Fermentation Stage | Butanol Production (g/L) | | Solvent Production (g/L) | | Solvent Productivity (g/L hr) | |
|---|---|---|---|---|---|---|
| | ATCC 4259 | ATCC 55025 | ATCC 4259 | ATCC 55025 | ATCC 4259 | ATCC 55025 |
| 1 | 0 | 0 | 0 | 0 | 0 | 0 |
| 2 | 4.7 | 6.8 | 7.3 | 10.3 | 0.63 | 0.90 |
| 3 | 8.7 | 11.6 | 13.3 | 18.0 | 0.70 | 0.95 |

| | Stage 1 | Stage 2 | Stage 3 |
|---|---|---|---|
| Dilution Rate ($^{-1}$) | 0.25 | 0.135 | 0.135 |
| pH: | 5.1 ± 0.1 | Uncontrolled | Uncontrolled |
| Temperature (°C.) | 36 | 36 | 36 |

EXAMPLE 2

The asporogenic strain (ATCC 55025) was further used in the fermentation configuration which consisted of three stage continuous fermentation followed by a batch fermentation. In this process configuration, the temperature of continuous stages was kept at 36° C. while batch fermentations were done at 24°, 27° and 30° C. After the establishment of steady-state continuous fermentation conditions, aliquots from the second and third stages were fermented under batch conditions to completion. The pH was controlled at 5 1±0.1 in first stage only with no pH control in stage two and three. The residence time in stage one was 4 hours whereas the residence time in stage two and three was 7.5 hours each.

The steady-state conditions established in the three stage continuous fermentation using the asporogenic strain are summarized in Table 3. A combined acetic and butyric acid concentration in stage one was 3.6 g/L with only 0.1 g/L solvents. Stage two contained 4.0 g/L acids and 11.1 g/L solvents after consumption of 44.3 g/L substrate. In stage three 3.2 g/L acids and 18.6 g/L solvents were produced.

TABLE 3

Three Stage Continuous Fermentation by Asporogenic C. acetobutylicum (ATCC 55025) Strain at Steady-State.

| Stage | Total Carbohydrates as glucose g/L | Fermentation Products (g/L) | | | | |
|---|---|---|---|---|---|---|
| | | Acetic Acid | Butyric Acid | Acetone | Butanol | Ethanol |
| Feed | 78.5 | — | — | — | — | — |
| Stage One | 61.2 | 0.8 | 2.8 | — | 0.1 | — |
| Stage Two | 34.2 | 1.7 | 2.3 | 3.2 | 7.1 | 0.8 |
| Stage Three | 26.5 | 1.8 | 1.4 | 5.0 | 11.8 | 1.8 |

Broth from stage two and three was batch fermented at different temperatures and the results are presented in Table 4.

TABLE 4

Batch fermentation of Stage Two and Three Broth from Continuous Fermentation Process Configuration described in Table 3, at different temperatures.

| Products/Substrate | Stage Two | | | Stage Three | | |
|---|---|---|---|---|---|---|
| | 24° C. | 27° C. | 30° C. | 24° C. | 27° C. | 30° C. |
| Products (g/L) | | | | | | |
| Acetic | 1.6 | 1.5 | 1.6 | 1.6 | 1.8 | 1.7 |
| Butyric | 0.1 | 0.1 | 0.1 | 0.2 | 0.2 | 0.4 |
| Acetone | 5.8 | 6.1 | 6.4 | 6.8 | 7.0 | 6.6 |
| Butanol | 17.7 | 18.5 | 17.6 | 18.5 | 18.4 | 17.3 |
| Ethanol | 3.5 | 3.4 | 3.4 | 3.3 | 3.2 | 3.0 |
| Total Solvents | 27.0 | 28.0 | 27.4 | 28.6 | 29.6 | 26.9 |
| Residual Carbohydrate Substrate (g/L) | 0 | 0 | 0 | 0 | 0 | 0 |

After batch fermentation of stage two broth at 24° C., 1.7 g/L acids and 27.0 g/L solvents were measured. A total of 78.5 g/L carbohydrate was consumed in 59.5 hours of total fermentation residence time. At 27° C., 1.6 g/L acids and 28.0 g/L solvents were measured with a substrate consumption of 78.5 g/L in a total residence time of 59.5 hours. At 30° C., 1.7 g/L acids and 27.4 g/L solvents were measured at the end of batch fermentation. The substrate consumption was 77.2 g/L in 59.5 hours total residence time. Effluent from stage three of the process configuration one was also batch fermented at 24°, 27° and 30° C. The batch fermentation at 24° C. produced 1.8 g/L acids and 28.6 g/L total solvents. At 27° C. batch fermentation 2.0 g/L acids and 29.6 g/L solvents were produced. After the batch fermentation at 30° C., however, 2.1 g/L acids and 26.9 g/L solvents were measured. At all the temperatures no residual substrate (from an initial substrate level of 78.5 g/L) was left after a total residence time of 67 hours.

The results indicate that with a multistage continuous process configuration followed by a batch fermentation at 27° C. for 48 hours a high butanol concentration of more than 18.0 g/L and total solvent concentration of approximately 30 g/L can be achieved provided an asporogenic strain is used for fermentation. Such high concentrations of solvents have not been reported earlier. Also, the intermediary butyric acid concentration measured was very low (0.1–0.2 g/L).

EXAMPLE 3

The asporogenic mutant strain (ATCC 39236) was used in this example. The temperature in each of the three continuous stages was 36° C. The residence times in the three stages were 4, 10 and 10 hours for stages one, two and three, respectively.

Table 5 shows the steady-state conditions for the three continuous stages. Stage two contained 7.4 g/L butanol and 11.7 g/L total solvents after 54.2 g/L of substrate had been consumed. The total fermentation residence time up to stage two was 14 hours. Stage three contained 12.0 g/L butanol and 18.4 g/L total solvents with a substrate consumption of 67.9 g/L. The total residence time up to stage three was 24 hours.

TABLE 5

Three-Stage Continuous Fermentation Asporogenic C. acetobutylicum (ATCC 39236) Strain.

| Stage | Total Carbohydrates as glucose g/L | Fermentation Products (g/L) | | | | |
|---|---|---|---|---|---|---|
| | | Acetic Acid | Butyric Acid | Acetone | Butanol | Ethanol |
| Feed | 82.2 | — | — | — | — | — |
| Stage One | 64.3 | 1.0 | 2.9 | <0.1 | <0.1 | — |
| Stage Two | 28.0 | 1.4 | 2.6 | 3.9 | 7.4 | 0.4 |
| Stage Three | 14.3 | 1.4 | 2.0 | 5.7 | 12.0 | 0.7 |

Table 6 shows the results of batch fermentations of the effluent from stages two and three for 48 hours at 24° C. and 30° C. A butanol concentration of 16.1 g/L and a total solvent concentration of 23.0 g/L were obtained after batch fermentation of the stage two broth at 24° C. About 72.7 g/L substrate was consumed after a total fermentation residence time of 62 hours. At a batch fermentor temperature of 30° C. a butanol concentration of 17.1 g/L and a total solvent concentration of 25.2 g/L were achieved. A total of 74.6 g/L substrate was consumed in a total fermentation residence time of 62 hours.

When the stage three effluents were batch fermented at 24° C. and 30° C. the substrate consumption did not go above a total of 73 g/L in either case. At 24° C. the butanol concentration reached 14.3 g/L with a total solvent concentration of only 21.5 g/L and the total residence time to consume 71.3 g/L substrate was 72 hours. At 30° C. the butanol concentration reaches 15.5 g/L with a total solvent concentration of 23.0 g/L and the total residence time to consume 72.7 g/L substrate was 72 hours.

The results indicate that under the conditions of Example 3 using the asporogenic mutant strain a maximum production of 17.1 g/L butanol and 25.2 g/L total solvents can be achieved if stage two fermentation effluent is batch fermented for 48 hours at 30° C. The asporogenic strain can grow with a substrate concentration higher than 80 g/L.

EXAMPLE 4

In this example the temperatures of the three stages were maintained at 36° C. but the residence times were changed from those of Example 3. The strain used was asporogenic mutant strain (ATCC 39236). The pH of the first stage was controlled at 5.1 and stage two and stage three had no pH control. The first stage residence time was 6.7 hours. The second and third stage retention times were each 16.7 hours. After the steady-state fermentation, effluents from stage two were batch fermented for 48 hours at 24° and 30° C.

Table 7 shows the acetic acid, butyric acid, acetone, butanol, ethanol and carbohydrate (as dextrose) concentration in each of the three continuous stages. The butanol concentration in stage three reached a concentration of 15.6 g/L with a substrate consumption of 74.5 g/L in 40 hours. A total of 24.6 g/L solvents were present in stage three with acetone accounting for 7.9 g/L. The respective concentration of acetone, butanol and total solvents in stage two were 6.3, 11.9 and 18.2 g/L.

TABLE 7

Three-Stage Continuous Fermentation by Asporogenic
C. acetobutylicum (ATCC 39236) Strain.

| Stage | Total Carbohydrates as glucose g/L | Fermentation Products (g/L) | | | | |
|---|---|---|---|---|---|---|
| | | Acetic Acid | Butyric Acid | Acetone | Butanol | Ethanol |
| Feed | 81.6 | — | — | — | — | — |
| Stage One | 43.3 | 2.4 | 4.4 | 1.2 | 1.9 | <0.1 |
| Stage Two | 14.5 | 2.3 | 3.2 | 6.3 | 11.9 | <0.1 |
| Stage Three | 7.1 | 1.8 | 1.8 | 7.9 | 15.6 | <1.1 |

TABLE 6

Batch Fermentation of Stage Two and Three
Effluents from Continuous Fermentation Process Configuration
described in Table 5, at Different Temperatures.

| | Stage Two | | Stage Three | |
|---|---|---|---|---|
| | 24° C. | 30° C. | 24° C. | 30° C. |
| Products (g/L) | | | | |
| Acetic Acid | 1.2 | 1.0 | 1.5 | 1.4 |
| Butyric Acid | 1.3 | 0.3 | 1.8 | 1.1 |
| Acetone | 5.6 | 4.8 | 6.2 | 6.4 |
| Butanol | 16.1 | 17.1 | 14.3 | 15.5 |
| Ethanol | 1.3 | 3.3 | 1.0 | 1.1 |
| Total Solvents | 23.0 | 25.2 | 21.5 | 23.0 |
| Substrate (g/L) | | | | |
| Residual Carbohydrate as Glucose | 9.5 | 7.6 | 10.9 | 9.5 |

Because the long retention times used in the continuous stages, the batch completion fermentations at 24° C. and 30° C. were conducted only for effluent from stage two. The results for these batch completion fermentations are presented in Table 8. The total solvents produced and carbohydrate consumed were the highest for the batch fermentation at 30° C. Butanol concentration of 16.7 g/1 and total solvents at 25.7 g/L were achieved at the end of 48 hours batch fermentation. However, after 24 hours batch fermentation and a total fermentation residence time of 47.4 hours the butanol concentration was 16.5 g/L, a total of 25.3 g/L solvents were produced and 80.5 g/L of carbohydrate was consumed.

TABLE 8

Batch fermentation of Stage Two Effluent from
Continuous Fermentation Process Configuration described in
Table 7 at Different Temperatures.

| | Stage Two | |
|---|---|---|
| | 24° C. | 30° C. |
| Products (g/L) | | |
| Acetic Acid | 2.1 | 2.3 |
| Butyric Acid | 2.1 | 1.5 |
| Acetone | 7.3 | 7.7 |
| Butanol | 15.3 | 16.7 |
| Ethanol | 1.1 | 1.3 |
| Total Solvents | 23.7 | 25.7 |
| Substrate (g/L) | | |
| Residual Carbohydrate as Glucose | 3.2 | 0.7 |

Thus, high butanol and total solvent concentrations are achievable by the asporogenic mutant strain in less than 50 hours by batch fermentation of the broth of stage two at 30° C.

EXAMPLE 5

This example also employed the sporeforming (ATCC 4259) and asporogenic strain (ATCC 55025) of C. acetobutylicum. The temperatures of continuous stage one, two and three were maintained at 36°, 36°, and 30° C., respectively. The residence time in stage one was 4 hours. The residence time in stages two and three was 7.5 hours each. The pH was controlled between 5.0 and 5.2 in stage one. The pH in stages two and three was not controlled. When the sporeforming strain (ATCC 4259) was used, batch fermentation of the effluent (fermentation broth) from stages two and three was carried out for 48 or 72 hours, at 27°, 30° and 36° C.

The results at steady-state conditions in the three stages are given in Table 9. At steady-state stage one had 2.4 g/L acids with traces of butanol. A combined acid concentration of 4.0 g/L and solvents concentration of 8.3 g/L was measured in stage two. Stage three had acid concentration of 3.8 g/L and solvents at 13.4 g/L at steady-state.

nol and 25.3 g/L solvent concentration in a multistage continuous temperature programmed fermentation under a process configuration of 36-36-30-30° C.

Fermentation performance of an asporogenic strain (ATCC 55025) was also examined under the same fermentation configuration to compare with the performance of sporeforming strain ATCC 4259. Broths of stage two and three were batch fermented at 24°, 27° and 30° C.

The steady-state conditions established in the three stage continuous fermentation for process configuration

TABLE 9

Three Stage Continuous Fermentation by Sporeforming *C. acetobutylicum* (ATCC 4259) Strain at Steady-State (36-36-30).

| Stage | Total Carbohydrates as glucose g/L | Fermentation Products (g/L) | | | | |
|---|---|---|---|---|---|---|
| | | Acetic Acid | Butyric Acid | Acetone | Butanol | Ethanol |
| Feed | 78.5 | — | — | — | — | — |
| Stage One | 63.0 | 0.5 | 1.9 | — | 0.1 | — |
| Stage Two | 38.2 | 1.5 | 2.5 | 2.5 | 5.2 | 0.6 |
| Stage Three | 28.1 | 1.6 | 2.2 | 4.2 | 8.5 | 0.7 |

The results obtained after batch finish of stage two and three broths are presented in Table 10.

TABLE 10

Batch Fermentation of Stage Two and Three Broth from Continuous Fermentation Process Configuration described in Table 9 at Different Temperatures for 48 hours.

| | Stage Two* | | | Stage Three** | |
|---|---|---|---|---|---|
| Products (g/L) | 36° C. | 30° C. | 27° C. | 36° C. | 30° C. |
| Acetic Acid | 1.9 | 1.8 | 1.8 | 1.9 | 1.6 |
| Butyric Acid | 0.1 | 0.2 | 0.1 | 0.8 | 0.1 |
| Acetone | 5.8 | 6.1 | 4.8 | 4.7 | 7.2 |
| Butanol | 12.6 | 15.6 | 16.0 | 10.8 | 16.7 |
| Ethanol | 1.1 | 1.9 | 1.6 | 0.9 | 1.4 |
| Total Solvents | 19.5 | 23.6 | 22.4 | 16.4 | 25.3 |
| Residual Carbohydrate Substrate (g/L) | 15.1 | 9.2 | 8.8 | 21.4 | 4.6 |

*Batch fermentation for 72 hours.
**Batch fermentation for 48 hours.

Batch fermentation of broth from stage two as well as three at 36° C. resulted in low butanol (12.6 and 10.8 g/L) and total solvent (19.5 and 16.4 g/L) concentrations. When stage two broth was batch fermented at 30° C., 15.6 g/L butanol and 23.6 g/L solvents were obtained after a substrate consumption of 69.3 g/L in a total residence time of 83.5 hours. When the stage two broth was fermented at 27° C., 16.0 g/L butanol and 22.4 solvents were achieved in the same residence time. Batch fermentation of stage three broth resulted in 16.7 g/L butanol and 25.3 g/L solvents after a substrate consumption of about 74 g/L in a total residence time of 67 hours. These results show that the sporeforming parent strain can produce a maximum of 16.7 g/L butatwo using an asporogenic strain (ATCC 55025) are summarized in Table 11. A combined acetic and butyric acid concentration in stage one was 3.6 g/L with only 0.2 g/L solvents. Stage two contained 4.2 g/L acids and 10.3 g/L solvents after consumption of 45 g/L substrate. In stage three 4.0 g/L acids and 18 g/L solvents were produced.

TABLE 11

Three Stage Continuous Fermentation by Asporogenic *C. acetobutylicum* (ATCC 55025) Strain at Steady-State (36-36-30).

| Stage | Total Carbohydrates as glucose g/L | Fermentation Products (g/L) | | | | |
|---|---|---|---|---|---|---|
| | | Acetic Acid | Butyric Acid | Acetone | Butanol | Ethanol |
| Feed | 78.5 | — | — | — | — | — |
| Stage One | 61.6 | 0.9 | 2.7 | 0.1 | 0.1 | — |
| Stage Two | 33.5 | 1.8 | 2.4 | 2.9 | 6.8 | 0.6 |
| Stage Three | 27.8 | 1.7 | 2.3 | 5.5 | 11.6 | 0.9 |

Broth from stage two was batch fermented and the results are presented in Table 12.

TABLE 12

Batch Fermentation of Stage Two and Three Broth of Process Configuration described in Table 11 at Different Temperatures for 48 hours.

| Products (g/L) | Stage Two | | | Stage Three | | |
|---|---|---|---|---|---|---|
| | 24° C. | 27° C. | 30° C. | 24° C. | 27° C. | 30° C. |
| Acetic Acid | 2.2 | 1.8 | 1.7 | 1.7 | 1.6 | 1.6 |
| Butyric Acid | 0.1 | 0.1 | 0.1 | 0.1 | 0.1 | 0.1 |
| Acetone | 6.5 | 6.0 | 6.0 | 6.9 | 7.0 | 6.4 |
| Butanol | 15.6 | 16.9 | 18.5 | 18.4 | 18.5 | 17.8 |
| Ethanol | 3.3 | 3.3 | 3.3 | 3.5 | 3.6 | 3.4 |
| Total Solvents | 25.4 | 26.2 | 27.8 | 28.8 | 29.1 | 27.6 |
| Residual Carbohydrate Substrate (g/L) | 7.3 | 3.4 | 0 | 0 | 0 | 1.1 |

Maximum butanol (18.5 g/L) and solvent (27.8 g/L) concentrations were obtained with batch fermentation at 30° C., while lowest butanol (15.6 g/L) and solvents (25.4 g/L) were obtained with batch finish at 24° C. in a total residence time of 59.5 hours.

Batch fermentation of stage three broth, however, resulted in maximum butanol (18.5 g/L) and solvent concentration (29.1 g/L) at 27° C. A total of 78.5 g/L substrate was consumed in 67 hours total residence time. At 30° C. batch fermentation only 17.8 g/L butanol and 27.6 g/L total solvents were obtained after substrate consumption of 77.4 g/L and residence time of 67 hours. No residual butyrate was left in the batch fermented broth at the end of fermentation.

These results indicate that an unexpected high butanol and total solvent concentrations are achieved with the asporogenic strain of *C. acetobutylicum* (ATCC 55025) when compared with sporeforming strain (ATCC 4259) using the same process configuration.

EXAMPLE 6

A sporeforming strain (ATCC 4259) and an asporogenic strain (ATCC 39236) of *C. acetobutylicum* were used for fermentation in this example. The first stage of the three continuous stages was maintained at 36° C. The second stage was kept at 30° C. and the temperature of the third stage was controlled at 27° C. The pH in the first stage was controlled between 5.0 and 5.2. The pH in stages two and three was not controlled. The residence time in stage one was 4 hours. The residence time in stages two and three was 10 hours in each. Broth from stage two and three were batch fermented at 24° C. and/or 30° C. for 72 hours for sporeforming strain and for 48 hours for asporogenic strain.

The steady-state conditions established in the three-stage continuous fermentation by sporeforming strain are summarized in Table 13. The combined butyric and acetic acid concentration in stage two reached 12.5 g/L and the solvent concentration was 0.8 g/L. In stage three an acid concentration of 13.1 g/L and a solvent concentration of 1.2 g/L was measured.

TABLE 13

Three-Stage Continuous Fermentation by Sporeforming *C. acetobutylicum* (ATCC 4259) Strain.

| Stage | Total Carbohydrates as glucose g/L | Fermentation Products (g/L) | | | | |
|---|---|---|---|---|---|---|
| | | Acetic Acid | Butyric Acid | Acetone | Butanol | Ethanol |
| Feed | 53.3 | — | — | — | — | — |
| Stage One | 33.2 | 2.3 | 6.1 | 0.1 | 0.3 | <0.1 |
| Stage Two | 27.8 | 3.4 | 9.1 | <0.1 | 0.8 | <0.1 |
| Stage Three | 22.5 | 3.3 | 9.8 | 0.4 | 0.8 | <0.1 |

Effluent from stage two was fermented in batch mode at 24° C. and 30° C. The results of these batch fermentations are presented in Table 14. After batch fermentation at 24° C., 14.5 g/L acid and 3.0 g/L solvent were measured with consumption of 35 g/L carbohydrate (or dextrose) in a total fermentation residence time of 86 hours. After batch fermentation at 30° C., 15.9 g/L acids and 2.5 g/L solvents were measured with consumption of 37.4 g/L carbohydrate (as dextrose) in a total fermentor residence time of 86 hours. Effluent from stage three was fermented in the batch mode at 24° C. Results at the end of 72 hours batch fermentation showed production of 14.3 g/L acids and 2.8 g/L solvents. A total of 35 g/L carbohydrate was consumed in a total fermentation time of 96 hours. The results show that the sporeforming strain does not produce significant amounts of solvents under the conditions of this example.

TABLE 14

Batch Fermentation of Stage Two and Three Broth from Continuous Process Configuration described in Table 13 at Different Temperatures.

| Products (g/L) | Stage Two | | Stage Three |
|---|---|---|---|
| | 24° C. | 30° C. | 24° C. |
| Acetic Acid | 3.5 | 4.0 | 3.5 |
| Butyric Acid | 11.0 | 11.9 | 10.8 |
| Acetone | 0.7 | 0.6 | 0.7 |
| Butanol | 2.1 | 1.7 | 1.9 |
| Ethanol | 0.1 | 0.2 | 0.2 |
| Total Solvents | 3.0 | 2.5 | 2.8 |
| Substrate (g/L) Residual Carbohydrate as Glucose | 18.3 | 15.9 | 18.3 |

Table 15 shows the steady-state conditions that were established in the three continuous stages by an asporogenic strain (ATCC 39236). The butanol concentration was 5.1 g/L with a total solvent concentration of 7.3 g/L in stage two; in 14 hours residence time, 42 g/L of substrate was consumed. In stage three the butanol and total solvent concentrations were 9.2 and 13.3 g/L, respectively, with a consumption of 50.9 g/L substrate in 24 hours.

TABLE 15

Three-Stage Continuous Fermentation by Asporogenic *C. acetobutyicum* (ATCC 39236) Strain.

| Stage | Total Carbohydrates as glucose g/L | Fermentation Products (g/L) | | | | |
|---|---|---|---|---|---|---|
| | | Acetic Acid | Butyric Acid | Acetone | Butanol | Ethanol |
| Feed | 80.1 | — | — | — | — | — |
| Stage One | 61.8 | 1.1 | 3.1 | <0.1 | <0.1 | <0.1 |
| Stage Two | 38.1 | 2.0 | 2.5 | 2.2 | 5.1 | <0.1 |
| Stage Three | 29.2 | 1.8 | 1.8 | 4.1 | 9.2 | <0.1 |

Table 16 shows the results of the batch fermentations of the stage two and stage three fermentation effluents for 48 hours. Batch fermentations of the stage two effluent produced a butanol concentration of 20.2 g/L with a total solvent concentration of 28.6 g/L. During a total residence time of 62 hours, 79.1 g/L of substrate was consumed. Batch fermentation at 30° C. resulted in a butanol concentration of 17.2 g/L and a total solvent concentration of 26.6 g/L being achieved. A total fermentor residence time of 62 hours was used to consume 75.6 g/L carbohydrates.

TABLE 16

Batch Fermentation of Stage Two and Three Effluents from Continuous Process Configuration described in Table 15 at Different Temperatures.

| Products (g/L) | Stage Two 24° C. | Stage Two 30° C. | Stage Three 24° C. |
|---|---|---|---|
| Acetic Acid | 1.2 | 1.4 | 1.2 |
| Butyric Acid | <0.1 | <0.1 | 0.1 |
| Acetone | 5.4 | 5.6 | 6.2 |
| Butanol | 20.2 | 17.2 | 19.6 |
| Ethanol | 3.0 | 3.8 | 1.9 |
| Total Solvents | 28.6 | 26.6 | 27.7 |
| Substrate (g/L) Residual Carbohydrate as Glucose | 1.0 | 4.5 | 0.6 |

After batch fermentation of the effluent from stage three at 24° C., a butanol concentration of 19.6 g/L and a total solvent concentration of 27.7 g/L were achieved. The total fermentation time was 72 hours to consume 79.5 g/L carbohydrate. This represents a butanol and total solvent productivity of 0.33 and 0.46 g/L hr, respectively. Butanol and solvent productivities were 0.39 and 0.54 g/L hr, respectively, at 48 hours of total fermentation when butanol concentration was 18.7 g/L with total solvents at 26.1 g/L.

These data indicate that when an asporogenic strain is used high butanol and high solvent concentrations with high productivities are achievable using the new process conditions.

EXAMPLE 7

This example used the asporogenic strain *C. acetobutylicum* (ATCC 39236). The temperature in the first stage was 36° C. with a residence time of 4 hours. The temperature was 30° C. in the second stage with a residence time of 12 hours. The temperature was 27° C. in the third stage with a residence time of 11.5 hours. The pH was controlled between 5.0 and 5.2 in the first stage, pH control was not used in the second or third stage. Effluents from stage two and three were batch fermented for 48 hours at 24° and/or 30° C.

The steady-state conditions established in this three-stage continuous fermentation are presented in Table 17. The second continuous stage had a butanol concentration of 7.9 g/L and a total solvent concentration of 12.4 g/L. The third stage had a butanol concentration of 12.1 g/L and a total solvent concentration of 18.8 g/L. In a residence time of 27.5 hours, 68 g/L carbohydrate were consumed.

TABLE 17

Three-Stage Continuous Fermentation by Asporogenic *C. acetobutyicum* (ATCC 39236) Strain.

| Stage | Total Carbohydrates as glucose g/L | Fermentation Products (g/L) Acetic Acid | Butyric Acid | Acetone | Butanol | Ethanol |
|---|---|---|---|---|---|---|
| Feed | 89.3 | — | — | — | — | — |
| Stage One | 65.4 | 1.1 | 3.3 | <0.1 | <0.1 | <0.1 |
| Stage Two | 34.6 | 1.4 | 3.1 | 4.1 | 7.9 | 0.4 |
| Stage Three | 21.3 | 1.3 | 3.0 | 6.0 | 12.1 | 0.7 |

Batch fermentation of stage two effluent at 24° C. resulted in a butanol concentration of 20.3 g/L with total solvents of 27.9 g/L and a substrate consumption of 85 g/L (Table 18). Batch fermentation at 30° C. resulted in a butanol concentration of 19.3 g/L and a total solvent concentration of 27.5 g/L in a total fermentor residence time of 75.5 hours with substrate consumption of 84 g/L. Stage three effluent was fermented in the batch mode at 24° C. After batch fermentation the butanol concentration was 20.0 g/L and the total solvent concentration was 28.2 g/L. The total fermentor residence time was 75.5 hours during which 87.4 g/L carbohydrate was consumed. The results are shown in Table 18.

TABLE 18

Batch Fermentation of Stage Two and Three Effluents from Continuous Process Configuration described in Table 17 at Different Temperatures.

| Products (g/L) | Stage Two 24° C. | Stage Two 30° C. | Stage Three 24° C. |
|---|---|---|---|
| Acetic Acid | 1.2 | 1.4 | 1.2 |
| Butyric Acid | 0.6 | 0.5 | 1.1 |
| Acetone | 5.7 | 6.0 | 6.8 |
| Butanol | 20.3 | 19.3 | 20.0 |
| Ethanol | 1.9 | 2.2 | 1.4 |
| Total Solvents | 27.9 | 27.5 | 28.2 |
| Substrate (g/L) Residual Carbohydrate as Glucose | 4.3 | 5.3 | 1.9 |

These results confirm that an asporogenic mutant strain achieves a high butanol and total solvents concentration using the process configuration described.

The foregoing examples show that unexpected results are obtained when asporogenic strains are used in a process including a temperature controlled, multistage continuous process, followed by batch fermentation. The examples also show that the reduction of temperature at appropriate stages of the process contributes to even higher solvent concentrations, and allows up to 88 g/L carbohydrate substrate to be consumed. This process is unique because of the high carbohydrate substrate concentration which can be consumed, the high solvent concentration broth which can be produced and the low concentration of organic acid byproducts in the final fermentation broth.

To achieve the economical production of solvents, such as butanol, from carbohydrates by fermentation with microorganisms a high yield, high productivity fermentation process, using a low cost media is necessary. Furthermore, a high end product concentration is very important for low cost recovery of the product. The process of the present invention represents a large improvement compared to the prior art. Pervaporation, using a selective membrane, can be used to vaporize the solvents from a solvent containing stream. Heat is required for the vaporization of products and liquid feeds to the pervaporation process can supply this heat. Integration of this energy efficient separation process with the fermentation process could provide the needed cooling for lowering the fermentation temperature as required for this fermentation process.

It will be apparent to those skilled in the art that a number of changes and modifications can be made without departing from the spirit and scope of the invention. Therefore, it is intended that the invention only be limited by the claims.

REFERENCES

1. Gibbs, D. F. 1983. The rise and fall (. . . and rise?) of acetone/butanol fermentations. Trends Biotechnol. 1:12-15.
2. Jones, D. T. and D. R. Woods. 1986. Acetone-butanol fermentation revisited. Microbiol. Rev. 50:484-524.
3. Bahl, H., W. Andersch, and G. Gottschalk. 1982. Continuous production of acetone and butanol by C. acetobutylicum in a two-stage phosphate limited chemostat. Eur. J. Appl. Microbiol. Biotechnol. 15:201-205.
4. Gottschalk, J. C. and J. G. Morris. 1982. Continuous production of acetone and butanol by Clostridium acetobutylicum growing in turbidostat culture. Biotechnol. Lett. 4:477-482.
5. Kim, B. H., P. Bellows, R. Datta and J. G. Zeikus. 1984. Control of carbon and electron flow in Clostridium acetobutylicum fermentation: utilization of carbon monoxide to inhibit hydrogen production and to enhance butanol yields. Appl. Environ. Microbiol. 48:764-770.
6. Afschar, A. S., H. Biebl, K. Schaller, and K. Schugerl. 1985. Production of acetone and butanol by Clostridium acetobutylicum in continuous culture with cell recycle. Eur. J. Appl. Microbiol. Biotechnol. 22:394-398.
7. Haggstrom, L. and S. O. Enfors. 1982. Continuous production of butanol with immobilized cells of Clostridium acetobutylicum. Appl. Biochem. Biotechnol. 7:35-37.
8. Prescott, S. C. and C. G. Dunn. 1959. The acetone-butanol fermentation, p. 250-284. In S. C. Prescott and C. G. Dunn (ed.), Industrial Microbiology, 3rd ed. McGraw Hill Book Co., New York.
9. L. A. Underkofler and R. J. Hickey, Eds. Chemical Publishing Co., New York, 1954. Chap. 11, pp. 347-390.
10. Moreira, A. R., A. C. Ulmer and J. C. Linden. 1981. Butanol toxicity in the butylic fermentation. Biotechnology and Bioengineering Symposium. 11:567-579.
11. McCutchan, W. N. and R. J. Hickey. 1954. The butanol-acetone fermentations. Ind. Ferment. 1:347-388.
12. McNeil, B. and B. Kristiansen. 1985. Effect of temperature upon growth rate and solvent production in batch cultures of Clostridium acetobutylicum. Biotech. Lett. 7(7):499-502.
13. Carnarius, E. H. 1940. Butyl alcohol fermentation process. U.S. Pat. No. 2,198,104. Commercial Solvents Corporation, Terre Haute, Indiana.
14. Compere, A. L. and W. L. Griffith. 1979. Dev. Ind. Microbiol. 20, 509.

We claim:

1. The improved process for the production of butanol, acetone and ethanol, by the fermentation of an asporogenic microorganism capable of producing butanol, acetone and ethanol upon a medium containing assimilable carbohydrate and nutrients which comprises conducting the fermentation in at least two continuous fermentors connected in series at a temperature of about 33° to about 38° C. at a pH of about 4.8 to about 5.5 to produce maximum growth of the microorganism and organic acids and then subjecting the effluent from the continuous fermentors to batch fermentation at a temperature of about 24° C. to about 30° C. to complete the fermentation.

2. A process of claim 1 in which the batch fermentation is conducted for up to about 72 hours.

3. A process of claim 1 in which the asporogenic microorganism has the identifying characteristics of C. acetobutylicum ATCC 39326.

4. A process of claim 1 in which the asporogenic microorganism has the identifying characteristics of C. acetobutylicum ATCC 55025.

* * * * *